United States Patent
Pamukcu et al.

(10) Patent No.: US 6,875,575 B1
(45) Date of Patent: Apr. 5, 2005

(54) DIAGNOSTIC METHODS FOR NEOPLASIA

(75) Inventors: Rifat Pamukcu, Spring House, PA (US); Gary A. Piazza, Doylestown, PA (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 09/902,948

(22) Filed: Jul. 11, 2001

Related U.S. Application Data

(63) Continuation of application No. 09/200,662, filed on Nov. 25, 1998, now abandoned.

(51) Int. Cl.$^7$ .............................................. G01N 33/53
(52) U.S. Cl. ..................... 435/7.1; 435/7.21; 435/7.23
(58) Field of Search .......................... 435/4, 7.1, 7.21, 435/7.23

(56) References Cited

U.S. PATENT DOCUMENTS

| | | | |
|---|---|---|---|
| 4,196,265 | A | 4/1980 | Koprowski et al. |
| 4,472,509 | A | 9/1984 | Gansow et al. |
| 5,021,236 | A | 6/1991 | Gries et al. |
| 5,401,774 | A | 3/1995 | Pamukcu et al. |
| 5,652,131 | A | 7/1997 | Beavo et al. |
| 5,696,159 | A | 12/1997 | Gross et al. |
| 5,702,936 | A | 12/1997 | Beavo et al. |
| 5,852,035 | A | 12/1998 | Pamukcu et al. |
| 5,858,694 | A | 1/1999 | Piazza et al. |
| 5,874,440 | A | 2/1999 | Pamukcu et al. |
| 6,130,053 | A * | 10/2000 | Thompson et al. |
| 6,156,528 | A * | 12/2000 | Pamukcu et al. |

FOREIGN PATENT DOCUMENTS

| | | |
|---|---|---|
| WO | WO 95 18969 A | 7/1995 |
| WO | WO 95/26743 | 10/1995 |
| WO | WO 98/14448 | 4/1998 |
| WO | WO 98/15530 | 4/1998 |
| WO | WO 98/16224 | 4/1998 |
| WO | WO 98/08848 | 5/1998 |
| WO | WO 96/32379 | 10/1998 |

OTHER PUBLICATIONS

J. Natl. Cancer Inst. 82: 1107–1112, 1990, "New Colorimetric Assay for Anticancer–Drug Screening".
Piazza, G.A., et al., Cancer Research, 55: 3110–16, 1995.
Steiner, A.L., Parker, C.W., Kipnis, D.M., J. Biol. Chem., 247(4):1106–13, 1971.
Harper, J., Brooker, G., Advances in Nucleotide Research, 10:1–33, 1979.
Waddell, W.R. et al., Am. J. Surgery, vol. 157, pp. 175–79 (1989).
Shen, T.Y. et al., Chemical and Biological Studies on Indomethacin, Sulindac and Their Analogs, pp. 107–178 (circa 1975).
Moorghen, M. et al., Journal of Pathology, vol. 156, pp. 341–347 (1988).
Moorghen, M. et al., Acta Histochemica, Suppl.–Band XXIX, S. 195–199 (1990).
Silvola, J. et al., Bts of nonsteroidal anti–inflammatory drugs on rastric mucosal phosphodiesterase activity, Agents and Actions, vol. 12.4, pp. 516–520 (1982).
Curtis–Prior, P.B. et al., Cyclic Nucleotide Phosphodiesterase Activity of Human Normal and Carbinomatous Lung Tissue, The Lancet, pp. 1225–1225 Dec. 4, 1876.
Makaryan, A.P. et al., Cyclic Nucleotides in Patients with Malignant Neoplasms of the Colon, Laboratornoe Delo, vol. 8, pp. 31–33 (1991).
Marcoz, P. et al. Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–35 (1993).
Radomski, Marek W. et al., Human Colorectal adenocarcinoma cells: differential nitric oxide synthesis determines their ability of aggregate platelets (Abstract Only), Cancer Res. 51(22) pp. 6073–8 (1991).
Lichtner, Rosemarie B., The pyrimidopyrimidine derivatives RA233 and TX–RA85 affect cell cycle distribution of two murine tumor cell lines (Abstract Only), Eur. J. Cancer Clin. Oncol. 25(6), pp. 945–51 (1989).
J.D. Gaffen et al., Increased killing of malignant cells by giving indomethacin with methotrexate, p. 30; column I; XP002084860 Chemical Abstract, vol. 106, No. 11, Mar. 16, 1987, abstract No. 78377, J.D.
Tsou, K–C, et al. 5'–Nucleotide Phosphodiesterase Isozyme–V as a Marker for Liver Metastases in Breast Cancer Patients, Cancer 54: 1788–1793, 1984.
Epstein P M et al; Dep. Pharmacol, Univ. Tex. Med. Sch., MD. Anderson Hosp., Houston, Tex. 88030, USA BIOSIS 78:140912, "Increased Cyclic Nucleotide Phospho DiEsterase Activity Associated With Proliferation and Cancer in Human and Murine Lymphoid Cells.
Stowe et al., "Changes in Rat Adrenal Cyclic Nucleotides During Normal and Neoplastic Growth." Biochimica et Biophysica Acta. 1977. vol. 497. pp. 690–701.
Hixson et al., "Antiproliferative Effect of Nonsteroidal Anti-inflammatory Drugs Against Human Colon Cancer Cells." Cancer Epidemiology, Biomarkers and Prevention. Jul.–Aug. 1994, vol. 3, pp. 433–438.
Silvola et al., "Effects of nonsteroidal antiinflammatory Drugs on rat gastric mucosal phosphodiesterase activity." Agents and Actions. 1982, vol. 12, pp. 516–520.
Giardiello et al., "Treatment of colonic and rectal adenomas with sulindac in familial adenomatous polyposis." New England Journal of Medicine. May 1993, vol. 328, pp. 1313–1316.

* cited by examiner

*Primary Examiner*—Sheela J. Huff
(74) *Attorney, Agent, or Firm*—Shu M. Lee

(57) ABSTRACT

This invention provides a method for diagnosing a patient with neoplasia.

6 Claims, 4 Drawing Sheets

DIAGNOSTIC METHODS FOR NEOPLASIA

This application is a Continuation of prior U.S. application Ser. No. 09/200,662 filed Nov. 25, 1998, now abandoned, entitled "Diagnostic Methods for Neoplasia," which is incorporated herein by reference.

BACKGROUND OF THE INVENTION

In recent years, new types of neoplasia inhibitors have been emerging. Such compounds selectively induce apoptosis (a form of cell death) in neoplastic, but not in normal cells. Neoplasia—which includes both precancerous and cancerous conditions—was historically treated chemotherapeutically only at the cancerous stage. Treatment with chemotherapeutics induced cell death (whether by apoptosis or necrosis) in rapidly proliferating cells indiscriminately (i.e., whether those cells were neoplastic or normal). As a result, most conventional chemotherapeutics caused significant cell death in normal tissues such as hair follicles, intestinal lining, skin and the like, that regenerate rapidly in the body. The side effects (e.g., hair loss, and skin and digestive disorders) of such conventional chemotherapeutics reflect non-specific cell death. As a result, conventional chemotherapeutics are used only on an acute (i.e., short-term) basis.

Because conventional chemotherapeutics non-specifically induce cell death, in both neoplastic and normal cells, such compounds, are not recommended for use against precancerous conditions even in patients with the most severe forms of precancerous conditions. For example, in familial polyposis patients—who can each form thousands of colonic polyps—surgical removal of the colon is standard practice (because of the extremely high cancer risk) whereas conventional chemotherapy is virtually unheard of.

As reported in pending U.S. patent application Ser. No. 09/664,035 filed Sep. 18, 2000 (Method For Identifying Compounds For Inhibition Of Cancerous Lesions, Pamukcu, et al. (Case No. P-119 CIP-3)), which is incorporated herein by reference, the selective neoplasia inhibitors described therein induce apoptosis in neoplastic cells, but not in normal proliferating cells. Thus, as reported in Ser. No. 09/664,035 (Case No. P-119 CIP-3), even patients with precancerous lesions can take such inhibitors without the side effects of conventional chemotherapeutics. Given the other attributes of such compounds, they can be taken by patients even on a chronic (i.e., long-term) basis. As reported in that application, a common attribute of such selective neoplasia inhibitors is that they inhibit cyclic GMP (cGMP)-specific phosphodiesterases (PDEs). cGMP-specific PDEs include the GMP-binding, cyclic GMP-specific phosphodiesterase (designated cGB-PDE) which is a phosphodiesterase gene family 5 isoenzyme (hereinafter "PDE5"). PDE5 is described more fully, inter alia, by Beavo, et al., in U.S. Pat. Nos. 5,652,131 and 5,702,936, that are incorporated herein by reference. Phosphodiesterase gene families 6 and 9 are also cGMP-specific isoforms. Another cGMP-specific PDE is the novel PDE found in neoplastic cells described by Liu, et al., in issued U.S. Pat. No. 6,200,771, entitled A Novel Cyclic GMP-Specific Phosphodiesterase And Methods For Using Same In Pharmaceutical Screening For Identifying Compounds For Inhibition Of Neoplastic Lesions (Case No. P-143), which is incorporated herein by reference. The novel cGMP-specific PDE described in that application is distinct from PDE5 and is broadly characterized by:

(a) cGMP specificity over cAMP;
(b) positive cooperative kinetic behavior in the presence of cGMP substrate;
(c) submicromolar affinity for cGMP; and
(d) insensitivity to incubation with purified cGMP-dependent protein kinase.

For general background on phosphodiesterases, see, Beavo, J. A. (1995) Cyclic Nucleotide Phosphodiesterases: Functional Implications of Multiple Isoforms, *Physiological Reviews* 75:725–747; and the web site <http://weber.u.washington.edu/~pde/pde.html>(November 1998).

BRIEF SUMMARY OF THE INVENTION

This invention involves methods of determining whether a patient with neoplasia has a type of neoplasia that is likely to respond to treatment with a cyclic GMP-specific PDE inhibitor.

In one aspect, this invention involves exposing a neoplastic tissue sample from a patient to a cyclic GMP-specific PDE inhibitor and monitoring whether the neoplastic tissue sample exhibits a sensitivity to treatment with that inhibitor.

In another aspect, this invention includes determining cyclic GMP-specific PDE activity in a neoplastic tissue sample. Detection of elevated cGMP-specific PDE activity in the neoplastic tissue sample is indicative that the neoplasia will respond to treatment with a cGMP-specific PDE inhibitor.

In another aspect, this invention includes the use of one or more antibodies that are immunoreactive with cGMP-specific PDEs to detect the presence of elevated cGMP-specific PDEs in a neoplastic tissue sample. Antibodies specific for cGMP-specific PDEs can be used in a variety of immunoassay methods, such as EIAs, ELISAs, or RIAs, to detect both the presence and the quantity of cGMP-specific PDEs in a tissue sample. The presence of elevated cGMP-specific PDE protein in the neoplastic tissue is indicative that the neoplasia will respond to treatment with a cGMP-specific PDE inhibitor.

In another aspect, this invention includes the use of nucleic acid detection techniques to detect mRNA encoding the production of cGMP-specific PDEs, among other things, in a neoplastic tissue sample. For example, reverse transcriptase polymerase chain reaction (RT-PCR) can be used to detect levels of messenger RNA (mRNA) of cGMP-specific PDEs in neoplastic tissue samples. The presence of cGMP-specific PDE mRNA is also indicative that the neoplasia will respond to treatment with a cGMP-specific PDE inhibitor.

In another aspect, this invention provides for diagnostic kits for ascertaining whether a particular neoplasia is a type of neoplasia that is likely to respond to treatment with a cGMP-specific PDE inhibitor. Diagnostic kits may be used, for example, to detect the level of cGMP-specific PDE protein or the level of mRNA encoding for cGMP-specific PDEs in a neoplastic tissue sample.

In another aspect, the cGMP-specific PDE inhibitor used in this invention has an inhibitory effect on at least PDE5 and the novel cGMP-specific PDE described hereinafter and in issued U.S. Pat. No. 6,200,771 (Case No. P-143) which is characterized by: (a) cGMP specificity over cAMP; (b) positive cooperative kinetic behavior in the presence of cGMP substrate; (c) submicromolar affinity for cGMP; and (d) insensitivity to incubation with purified cGMP-dependent protein kinase.

DETAILED DESCRIPTION OF THE INVENTION

Figure 1:
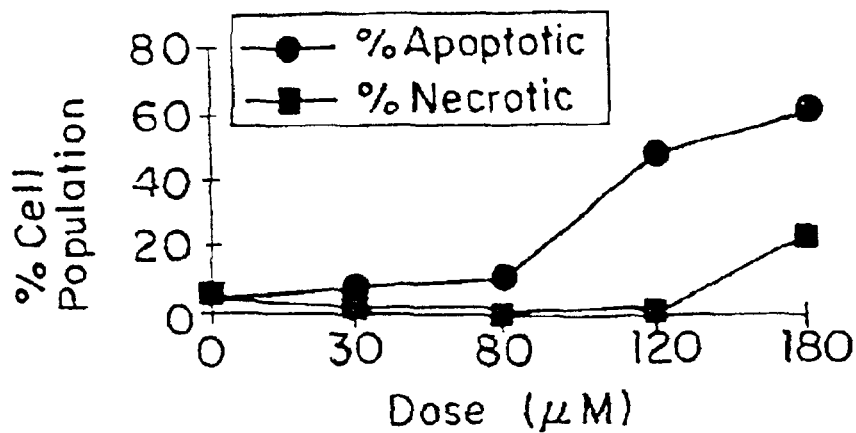
FIG. 1 illustrates the effects of sulindac sulfide and exisulind on apoptosis and necrosis of HT-29 cells.
Figure 1:
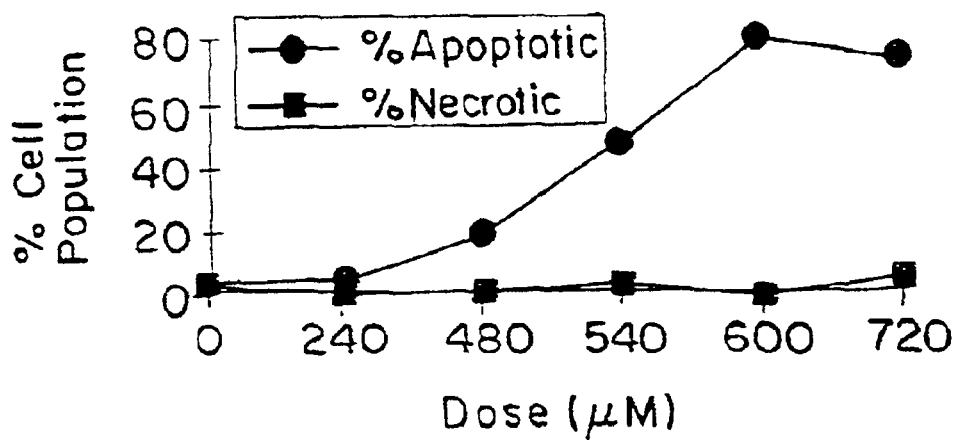

This invention involves diagnostic methods to determine whether a patient with neoplasia has a type of neoplasia that is likely to respond to treatment with a cGMP-specific PDE inhibitor. As mentioned above, there are a new class of inhibitors that induce apoptosis in neoplastic tissues, but not in normal tissues. The inhibition of cyclic GMP-specific PDEs, including PDE5 and the novel PDE described below, with such inhibitors is a powerful new tool in the treatment neoplasia.

I. Inhibition of Cell Growth

To determine whether a patient has a type of neoplasia that is likely to respond to treatment with a cGMP-specific PDE inhibitor, a neoplastic tissue sample from the patient is exposed to such an inhibitor and is tested to determine whether the neoplastic tissue sample exhibits sensitivity to treatment with the cGMP-specific PDE inhibitor.

For example, in a patient with familial polyposis, a suspected neoplastic tissue sample is obtained, processed, and cultured in appropriate tissue culture medium and conditions in the presence and absence of a cGMP-specific PDE inhibitor to determine whether the neoplastic tissue sample is sensitive to treatment with such an inhibitor. Sensitivity to a cGMP-specific PDE inhibitor can be characterized by growth inhibition or by an increase in apoptosis in the neoplastic cells treated with the inhibitor, relative to the untreated tissue sample.

In one embodiment, the diagnostic method of this invention involves determining whether a neoplastic tissue sample is responsive to treatment with a cGMP-specific PDE inhibitor by exposing the neoplastic tissue sample to a cGMP-specific PDE inhibitor and determining whether such treatment reduces the growth of tumor cells in vitro.

Briefly, suspected neoplastic tissue samples are removed from a patient and grown as explants in vitro. The tissue samples are grown in the presence and absence of a cGMP-specific PDE inhibitor. After being grown in culture, cells are fixed by the addition of cold trichloroacetic acid. Protein levels are measured using the sulforhodamine B (SRB) colorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," *J. Natl. Cancer Inst.* 82: 1107–1112, 1990, which is incorporated herein by reference.

In addition to the SRB assay, a number of other methods are available to measure growth inhibition and can be used instead of the SRB assay. These methods include counting viable cells following trypan blue staining, labeling cells capable of DNA synthesis with BrdU or radiolabeled thymidine, neutral red staining of viable cells, or MTT staining of viable cells.

Inhibition of cell growth indicates that the neoplasia in question is sensitive to cGMP-specific PDE inhibitors. Inhibition of cell growth is indicative that the patient would be an appropriate candidate for treatment with a cGMP-specific PDE inhibitor.

As described by Pamukcu, et al., in the pending U.S. patent application Ser. No. 09/664,035 (Case No. P-119 CIP-3)), a number of compounds potentially useful as PDE inhibitors in the diagnostic method of this invention were tested on a number of neoplastic cell lines representing various cell types. For example, these cell lines include: SW-480—colonic adenocarcinoma; HT-29—colonic adenocarcinoma; A-427—lung adenocarcinoma; MCF-7—breast adenocarcinoma; UACC-375—melanoma line; and DU145—prostrate carcinoma. Growth inhibition data obtained using these cell lines indicate an inhibitory effect by cGMP-specific PDE inhibitors on neoplastic lesions. These cell lines are well characterized, and are used by the United States National Cancer Institute in their screening program for new anti-cancer drugs.

To show the effectiveness of cGMP-specific PDE inhibition on various forms of neoplasia, (and, therefore, the usefulness of the diagnostic methods of this invention) cGMP-specific PDE inhibitors were tested on a number of neoplastic cell lines. The effects of sulindac sulfide and exisulind, two cGMP-specific PDE inhibitors, were determined. Exisulind is defined as (Z)-5-fluoro-2-methyl-1-[[4-(methylsulfonyl)phenyl]methylene]indene-3-yl acetic acid or a salt thereof. (See, Pamukcu and Brendel, U.S. Pat. No. 5,401,774.) The data are shown in Table 1 below. The $IC_{50}$ values were determined by the SRB assay. These data indicate that such cGMP-specific PDE inhibitors are effective in the treatment of neoplastic conditions.

TABLE 1

| Growth Inhibitory Data of Various Cell Lines | | |
|---|---|---|
| Cell Type/ | $IC_{50}$ ($\mu M$)* | |
| Tissue specificity | Sulindac sulfide | Exisulind |
| HT-29, Colon | 60 | 120 |
| HCT116, Colon | 45 | 90 |
| MCF7/S, Breast | 30 | 90 |
| UACC375, Melanoma | 50 | 100 |
| A-427, Lung | 90 | 130 |
| Bronchial Epithelial Cells | 30 | 90 |
| NRK, Kidney (non ras-transformed) | 50 | 180 |
| KNRK, Kidney (ras transformed) | 60 | 240 |
| Human Prostate Carcinoma PC3 | | 82 |

*Determined by neutral red assay as described by Schmid et al., in Proc. AACR Vol 39, p. 195 (1998).

II. Apoptosis

In another aspect of the diagnostic method of this invention, sensitivity of a neoplastic tissue to treatment with a cGMP-specific PDE inhibitor is tested with an apoptosis assay. For example, a suspected neoplastic tissue sample is processed and exposed to a cGMP-specific PDE inhibitor. Sensitivity to a cGMP-specific PDE inhibitor is characterized by an increase in apoptosis in the neoplastic tissue sample treated with the inhibitor relative to the untreated tissue sample.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blebbing, condensation of cytoplasm, and the activation of endogenous endonucleases.

Apoptosis occurs naturally during normal tissue turnover and during embryonic development of organs and limbs. Apoptosis also is induced by cytotoxic T-lymphocytes and natural killer cells, by ionizing radiation, and by certain chemotherapeutic drugs. Inappropriate regulation of apoptosis is thought to play an important role in many pathological conditions including cancer, AIDS, Alzheimer's disease, etc. Patients with neoplasias that exhibit an increase in cell death through apoptosis after treatment with a cGMP-specific PDE inhibitor are candidates for treatment with a cGMP-specific PDE inhibitor.

In one type of apoptosis assay, suspected neoplastic cells are removed from a patient. The cells are then grown in culture in the presence or absence of a cGMP-specific PDE inhibitor. Apoptotic cells are measured by combining both the attached and "floating" compartments of the cultures. The protocol for treating tumor cell cultures with PDE inhibitors and related compounds to obtain a significant amount of apoptosis has been described in the literature. (See, Piazza, G. A., et al., *Cancer Research*, 55:3110–16, 1995, which is incorporated herein by reference). The novel features of this assay include collecting both floating and attached cells, identification of the optimal treatment times and dose range for observing apoptosis, and identification of optimal cell culture conditions.

A. Analysis of Apoptosis by Morphological Observation

Following treatment of neoplastic and normal cells with a test compound, cultures can be assayed for apoptosis and necrosis by fluorescent microscopy following labeling with acridine orange and ethidium bromide. The method for measuring apoptotic cell number has previously been described by Duke & Cohen, "Morphological And Biochemical Assays Of Apoptosis," *Current Protocols In Immunology*, Coligan et al., eds., 3.17.1–3.17.16 (1992, which is incorporated herein by reference).

For example, floating and attached cells are collected, and aliquots of cells are centrifuged. The cell pellet is then resuspended in media and a dye mixture containing acridine orange and ethidium bromide. The mixture is then examined microscopically for morphological features of apoptosis.

B. Analysis of Apoptosis by DNA Fragmentation

Apoptosis can also be quantified by measuring an increase in DNA fragmentation in cells which have been treated with cGMP-specific PDE inhibitors. Commercial photometric EIAs for the quantitative in vitro determination of cytoplasmic histone-associated-DNA-fragments (mono- and oligonucleosomes) are available (Cell Death Detection ELISA$^{plus}$, Cat. No. 1,774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligo-nucleosomes in the cytoplasmic fraction of cell lysates.

According to the vendor, apoptosis is measured in the following fashion. The sample (cell-lysate) is placed into a streptavidin-coated microtiter plate (MTP). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by washing, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

C. Apoptosis Assay

Increases in apoptosis are indicative that the neoplasia in question is sensitive to treatment with a cGMP-specific PDE inhibitor.

A colon carcinoma cell line, HT-29, was treated with the c-GMP-specific PDE inhibitors, sulindac sulfide and exisulind in accordance with the protocols for the assay mentioned above. (See, Piazza, G. A., et al., *Cancer Research*, 55:3110–16, 1995.) In accordance with those protocols, FIG. 1 shows the effects of sulindac sulfide and exisulind on apoptotic and necrotic cell death. HT-29 cells were treated for six days with the indicated dose of either sulindac sulfide or exisulind. Apoptotic and necrotic cell death was determined as previously described (Duke and Cohen, In: Current Protocols in Immunology, 3.17.1–3.17.16, New York, John Wiley and Sons, 1992). The data show that both sulindac sulfide and exisulind are capable of causing apoptotic cell death without inducing neoplastic cell necrosis. All data were collected from the same experiment.

Figure 2:
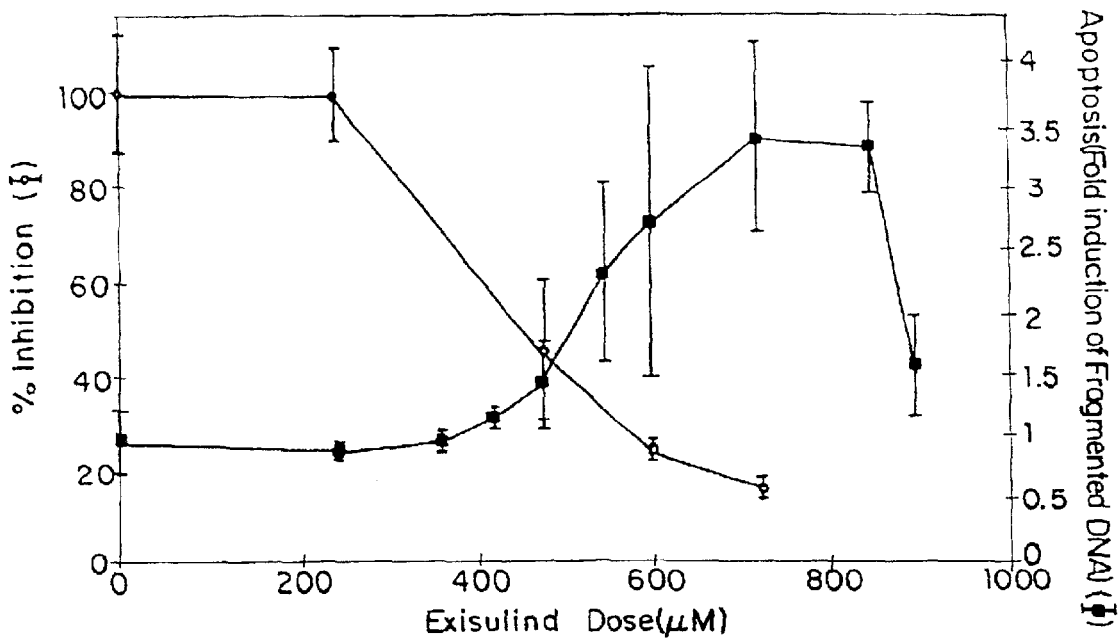
FIG. 2 illustrates the effects of sulindac sulfide and exisulind on HT-29 cell growth inhibition and apoptosis induction as determined by DNA fragmentation.
Figure 2:
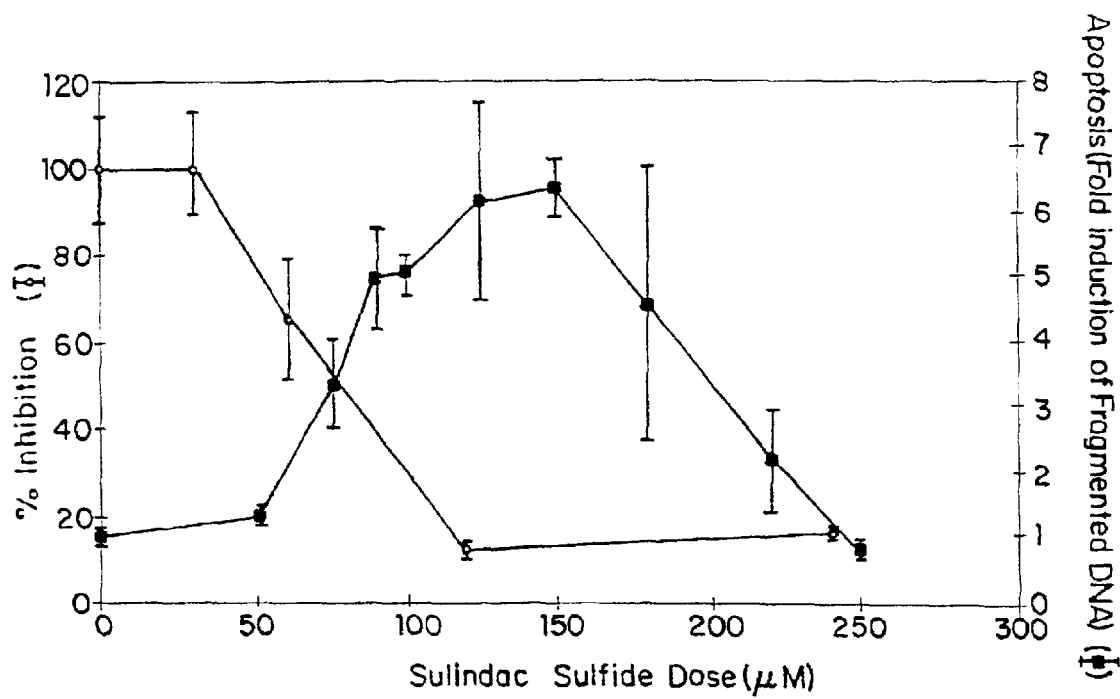

FIG. 2 shows the effect of sulindac sulfide and exisulind on tumor growth inhibition and apoptosis induction as determined by DNA fragmentation. The top FIG. (2A) shows growth inhibition (open symbols, left axis) and DNA fragmentation (closed symbols, right axis) by exisulind. Bottom FIG. (2B) shows growth inhibition (open symbols) and DNA fragmentation (closed symbols) by sulindac sulfide. Growth inhibition was determined by the SRB assay after six days of treatment. DNA fragmentation was determined after 48 hours of treatment. All data was collected from the same experiment The diagnostic method of this invention is used to determine whether a particular neoplasia is sensitive to treatment with a cGMP-specific PDE inhibitor. The apoptosis inducing activity for a series of phosphodiesterase inhibitors, specific for different PDEs, was determined. The data are shown in Table 2 below. HT-29 cells were treated for 6 days with various inhibitors of phosphodiesterase. Apoptosis and necrosis were determined morphologically after acridine orange and ethidium bromide labeling in accordance with the assay described, supra. The data show cGMP-specific PDE inhibition represents a unique and valuable pathway to induce apoptosis in neoplastic cells.

TABLE 2

Apoptosis Induction Data for PDE Inhibitors

| Inhibitor | Reported Selectivity | % Apoptosis | % Necrosis |
|---|---|---|---|
| Vehicle | | 8 | 6 |
| 8-methoxy-IBMX | PDE1 | 2 | 1 |
| Milrinone | PDE3 | 18 | 0 |
| RO-20-1724 | PDE4 | 11 | 2 |
| MY5445 | PDE5 | 80 | 5 |
| IBMX | Non-selective | 4 | 13 |

D. Apoptosis Clinical Study

Increases in apoptosis are indicative that the neoplasia in question is sensitive to treatment with a cGMP-specific PDE inhibitor, such as sulindac sulfone (aposulind). A human in vivo aposulind-induced selective induction of apoptosis in colonic polyps is described below. Six familial polyposis patients per group were administered one of three doses of aposulind (200 mg, 400 mg which was later lowered to 200 mg for most patients in the group, or 300 mg) twice daily (BID).

1. Methods

Biopsies are taken from patients and used to investigate possible cellular mechanisms of apoptosis. Biopsy samples are placed in transfer media (500 ml RPMI 1640 containing 50 ml fetal calf serum, $5 \times 10^8$ units penicillin G, and $5 \times 10^6$ µg streptomycin) and kept on ice for less than 1 hour until transfer to the pathology department. Upon receipt in the pathology department, samples are removed from the transfer media and oriented mucosa up, serosa down on filter paper, placed between biopsy sponges in a tissue cassette, and fixed in 10% neutral buffered formalin for 24 hours. Samples are then transferred to 70% ethanol and embedded in paraffin. Samples are oriented perpendicularly to the tissue cassette during final orientation in paraffin for longitudinal crypt exposure and easy visualization of mucosa and the relation to the basement membrane.

Four micron sections of tissue were cut, mounted, deparaffinized, rehydrated in graded alcohol, and treated with pepsin (5 mg/ml) to digest protein in the tissue. Sections were washed and treated with 2% hydrogen peroxide ($H_2O_2$) in PBS to quench endogenous peroxidase and washed again. Tissue samples were then circled with a PAP pen (Research Products Int., 800-323-9814) to produce a hydrophobic barrier to concentrate reagents on the sample. If a DNase positive control is desired, the sample is treated with DNase for 10 minutes, equilibrated in transferase buffer, and treated using 100 enzyme units/ml terminal transferase enzyme (TdT) at 37° C. for 60 minutes. Samples are washed and anti-digoxigenin-peroxidase is applied. Each sample is then covered with a coverslip and left in a humid box at room temperature for 30 minutes. After washing three times peroxidase is developed using DAB for nine minutes. After sufficient color development, the slides are washed and counterstained with hemotoxylin and eosin.

Apoptotic and nonapoptotic cells are counted on the basis of staining and morphology. An apoptotic labeling index (ALI) is calculated by dividing the total number of apoptotic cells counted by the total number of epithelial cells counted and expressing the quotient as a percentage.

2. Results

Baseline ALI were measured in both normal samples and paired polyp samples. Baseline ALI in normal tissue was determined to be 0.61%±0.05 (mean±SEM), a nine fold lower level of apoptosis than in polyp samples which had a mean apoptotic level of 5.60%±0.74. (Table 3).

TABLE 3

| Pt. ID# | Baseline | |
| --- | --- | --- |
| | Weighted % Normal | Weighted % Dysplasia |
| 1001 | 0.76% | 1.89% |
| 1002 | 0.56% | 3.00% |
| 1005 | 0.77% | |
| 1006 | 0.46% | 3.78% |
| 1007 | 0.43% | 5.81% |
| 1008 | 0.75% | 8.14% |
| 2001 | 0.73% | 1.71% |
| 2002 | 0.63% | 9.91% |
| 2003 | 0.63% | 4.13% |
| 2006 | 0.35% | 4.13% |
| 2007 | 0.95% | 5.33% |

TABLE 3-continued

| Pt. ID# | Baseline | |
| --- | --- | --- |
| | Weighted % Normal | Weighted % Dysplasia |
| 2008 | | |
| 5001 | 0.71% | 7.78% |
| 5004 | 0.71% | 7.49% |
| 5006 | 0.19% | 7.01% |
| 5007 | 0.66% | |
| 5009 | 0.28% | 2.88% |
| 5010 | 0.83% | 11.02% |
| Mean | 0.61200488 | 5.600163764 |
| S.E. | 0.05% | 0.74% |
| | n = 17 patients | n = 15 patients |

There was no significant change in normal mucosa ALI versus baseline ALI during treatment over time for any of the treatment groups. However, dysplastic tissue taken from patients in the 400/200 mg BID group demonstrated a two-fold elevation in ALI following drug treatment when the group was uniformly dosed at 400 mg BID. A two fold increase in ALI was also noted in polyps following six months of treatment on the 300 mg BID dose. The 200 mg BID group did not demonstrate any elevation in ALI following treatment with aposulind. (Table 4).

TABLE 4

Mean Polyp ALI over Treatment

| | Mean ALI | St. Error |
| --- | --- | --- |
| 200 Month 0 | 4.52% | 1.11% |
| 200 Month 1 | 4.05% | 1.05% |
| 200 Month 4 | 4.52% | 0.70% |
| 200 Month 6 | 5.90% | 1.07% |
| 400/200 Month 0 | 5.04% | 1.35% |
| 400/200 Month 1 | 10.98% | 2.79% |
| 400/200 Month 4 | 5.51% | 1.33% |
| 400/200 Month 6 | 5.10% | 0.68% |
| 300 Month 0 | 7.24% | 1.45% |
| 300 Month 1 | 4.90% | 1.64% |
| 300 Month 4 | | |
| 300 Month 6 | 15.63% | 4.50% |

This study shows that over six months of treatment, apoptosis levels are doubled in regressing polyps, and indicates that aposulind, a cGMP-specific PDE inhibitor can effectively induce the regression of neoplasia, such as adenomatous lesions, by apoptosis. This selective induction of apoptosis in polyps by aposulind and the accompanying diminution of polyp size and decrease in polyp number is an important discovery for the treatment of neoplasias.

III. Phosphodiesterase Activity

A. Phosphodiesterase Enzyme Assay

In one embodiment of this invention, the presence of cGMP-specific PDEs in a neoplastic tissue sample is determined by performing a phosphodiesterase enzyme assay. If cGMP-specific PDE activity is elevated in a neoplastic tissue sample, compared to cGMP-specific PDE activity in normal tissue, it is indicative that the neoplasia in question can be treated with a cGMP-specific PDE inhibitor. The normal tissue used in this assay, and in the other assays described herein which employ normal tissue, is optionally from the same patient as the neoplastic tissue sample or from a reference standard which may be based on a population of patients, and optionally is the same type of tissue as the neoplastic tissue. Additionally, if the neoplastic cells in a sample are exposed to an antineoplastic cGMP-specific PDE inhibitor and the cGMP-specific hydrolytic activity of the sample decreases, it is further indicative that the neoplasia in question is a candidate for treatment with a cGMP-specific PDE inhibitor.

Phosphodiesterase activity (whether in a mixture or separately) can be determined using methods known in the art, such as a method using a radioactively labeled form of cGMP as a substrate for the hydrolysis reaction. Cyclic GMP labeled with tritium ($^3$H-cGMP) is used as the substrate for the PDE enzymes. (Thompson, W. J., Teraski, W. L., Epstein, P. M., Strada, S. J., *Advances in Cyclic Nucleotide Research*, 10:69–92, 1979, which is incorporated herein by reference). In this assay, cGMP-PDE activity is determined by quantifying the amount of cGMP substrate that is hydrolyzed either in the presence or absence of a cGMP-specific PDE inhibitor.

In brief, a solution of defined substrate $^3$H-cGMP specific activity is mixed with a cGMP-specific PDE inhibitor. The control sample contains no inhibitor. The mixture is incubated with cell lysates from neoplastic tissue samples. The degree of phosphodiesterase inhibition is determined by calculating the amount of radioactivity released in samples that include a cGMP-specific PDE inhibitor and comparing those against a control sample which contains no inhibitor.

B. Cyclic Nucleotide Measurements

Alternatively, the sensitivity of a neoplastic tissue sample to treatment with a cGMP-specific PDE inhibitor is reflected by an increase in the levels of cGMP in neoplastic cells exposed to the cGMP-specific PDE inhibitor. The amount of PDE activity can be determined by assaying for the amount of cyclic GMP in the extract of neoplastic cells treated with a cGMP-specific PDE inhibitor using a radioimmunoassay (RIA). In this procedure, cells from a neoplastic tissue are incubated with a cGMP-specific PDE inhibitor. After about 24 to 48 hours, the cells are solubilized, and cyclic GMP is purified from the cell extracts. The cGMP is acetylated according to published procedures, such as using acetic anhydride in triethylarnine (Steiner, A. L., Parker, C. W., Kipnis, D. M., *J. Biol. Chem.*, 247(4): 1106–13, 1971, which is incorporated herein by reference). The acetylated cGMP is quantitated using radioimmunoassay procedures (Harper, J., Brooker, G., *Advances in Nucleotide Research*, 10: 1–33, 1979, which is incorporated herein by reference).

In addition to observing increases in the content of cGMP in neoplastic cells as a result of treatment with a cGMP-specific PDE inhibitor, decreases in the content of cAMP have also been observed. It has been observed that treatment of a neoplastic tissue sample with a cGMP-specific PDE inhibitor initially result in an increased cGMP content within minutes, and secondarily, there is a decreased cAMP content within 24 hours. To determine the cyclic AMP content in cell extracts, radioimmunoassay techniques similar to those described above for cGMP are used.

IV. Antibody Techniques

In another aspect, the present invention includes the use of one or more antibodies that are immunoreactive with cGMP-specific PDEs. Antibodies that are immunoreactive with cGMP-specific PDEs specifically recognize and bind to cGMP-specific PDEs. Antibodies reactive to cGMP-specific PDEs are used to detect and quantify the various cGMP-specific PDEs present in a suspected neoplastic tissue sample. The presence of cGMP-specific PDEs in a neoplastic tissue sample is indicative that the particular neoplasia is a candidate for treatment with a cGMP-specific PDE inhibitor.

Antibodies can be generated individually against PDE5, individually against the novel cGMP-specific PDE described below and in issued U.S. Pat. No. 6,200,771 (Case No. P-143), or they can be generated against a mixture of cGMP-specific phosphodiesterases, including PDE5 and the novel cGMP-specific PDE. Means for preparing and characterizing antibodies are well known in the art. (See, e.g., Antibodies: A Laboratory Manual, Cold Spring Harbor Laboratory, 1988, which is incorporated herein by reference.)

A. Antibody Generation

1. Polyclonal Antibodies

Antibodies can be either polyclonal or monoclonal. Briefly, a polyclonal antibody is prepared by immunizing an animal with immunogenic protein or polypeptide and collecting antisera from that immunized animal. A wide range of animal species are used for the production of antisera, and the choice is based on the phylogenetic relationship to the antigen. Typically the animal used for production of anti-antisera is a rabbit, a guinea pig, a chicken, a goat, or a sheep. Because of the relatively large blood volume of sheep and goats, these animals are preferred choices for production of polyclonal antibodies.

As is well known in the art, a given antigenic composition may vary in its ability to generate an immune response. It is often necessary, therefore, to boost the host immune system by coupling a peptide or polypeptide immunogen to a carrier. Examples of common carriers are keyhole limpet hemocyanin (KLH) and bovine serum albumin (BSA). Means for conjugating a polypeptide to a carrier protein are well known in the art and include MBS [m-Malecimidobenzoyl-N-hydroxysuccimide ester], EDAC [1-ethyl-3-(3-Dimethylaminopropyl) carbodiimide hydrochloride], and bisdiazotized benzidine.

As is also well known in the art, the immunogenicity of a particular composition can be enhanced by the use of non-specific stimulators of the immune response, known as adjuvants. Cytokines, toxins or synthetic compositions may also be used as adjuvants. The most commonly used adjuvants include complete Freund's adjuvant (a non-specific stimulator of the immune response containing killed *Mycobacterium tuberculosis*) and incomplete Freund's adjuvant.

Milligram quantities of antigen are preferred although the amount of antigen administered to produce polyclonal antibodies varies upon the nature and composition of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate monoclonal antibodies (MAbs).

For production of rabbit polyclonal antibodies, the animal can be bled through an ear vein or alternatively by cardiac puncture. The removed blood is allowed to coagulate and then centrifuged to separate serum components from whole cells and blood clots. Sterility is maintained throughout this preparation. The serum may be used as is for various applications or else the desired antibody fraction may be purified by well-known methods, such as affinity chromatography using another antibody, a peptide bound to a solid matrix, or by using, e.g., protein A or protein G chromatography.

2. Monoclonal Antibodies

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain. The immunizing composition is administered in a manner effective to stimulate antibody producing cells.

The methods for generating monoclonal antibodies (MAbs) generally begin along the same lines as those for preparing polyclonal antibodies. Rodents such as mice and rates are preferred animals, however, the use of rabbit, sheep, or frog cells is also possible. The use of rats may provide certain advantages (Goding, In: Monoclonal Antibodies: Principles and Practice, 2d ed., 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen is typically mixed with adjuvant, such as Freund's complete or incomplete adjuvant. Booster injections with the same antigen are made at approximately two week intervals.

Following immunization, somatic cells with the potential for producing antibodies, specifically B lymphocytes (B cells), are selected for use in the MAb generating protocol. Antibody-producing B cells are usually obtained by disbursement of the spleen, but tonsil, lymph nodes, or peripheral blood may also be used. Spleen cells are preferred because they are a rich source of antibody-producing cells that are in the dividing plasmablast stage.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). Any one of a number of myeloma cells may be used, as is known to those of skill in the art (Goding, pp. 65–66, 1986).

Methods for generating hybrids of antibody-producing spleen or lymph node cells and myeloma cells usually comprise mixing somatic cells with myeloma cells in about a 2:1 proportion in the presence of an agent or agents (chemical or electrical) that promote the fusion of cell membranes, The original fusion method using Sendai virus has largely been replaced by those using polyethylene glycol (PEG), such as 37% (v/v) PEG, as has been described in the art. The use of electrically-induced fusion methods is also appropriate.

Fusion procedures usually produce viable hybrids at low frequencies. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which particular clones are selected. The selection of hybridomas is performed by culturing the cells in microtiter plates, followed by testing the individual clonal supernatants (after about two to three weeks) for antibody producers using ELISA IgG assays. Antibody positive hybridomas are screened further for MAbs with the desired reactivity using antigen based assays. Such assays are normally sensitive, simple, and rapid, such as radioimmunoassays, enzyme immunoassays, dot immunobinding assays, and the like.

The selected hybridomas are then serially diluted and cloned into individual antibody-producing cell lines, clones of which are then propagated indefinitely to provide MAbs. The cell lines can be exploited for MAb production in two basic ways.

A sample of the hybridoma can be injected (often into the peritoneal cavity) into a histo-compatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the antibody producing hybridoma. The ascites fluid of the animal, and in some cases blood, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography.

3. Antibody Conjugates

The present invention further provides antibodies against GMP-specific PDE proteins that are linked to one or more other agents to form an antibody conjugate. Any antibody of sufficient selectivity, specificity, and affinity may be employed as the basis for an antibody conjugate.

Certain examples of antibody conjugates are those conjugates in which the antibody is linked to a detectable label. "detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins." In the context of the present invention, immunotoxins are generally less preferred.

Antibody conjugates are thus preferred for use as diagnostic agents. Antibody diagnostics generally fall within two classes, those for use in in vitro diagnostics, such as in a variety of immunoassays, and those for use in in vivo diagnostic protocols, generally known as "antibody-directed imaging."

Many appropriate imaging agents are known in the art, as are methods for their attachment to antibodies (see, e.g., U.S. Pat. Nos. 5,021,236 and 4,472,509, both incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. Fluorescent labels include rhodamine, fluorescein isothiocyanate and renographin.

The preferred antibody conjugates for diagnostic use in the present invention are those intended for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds.

B. Immunoassays

In another aspect, the present invention concerns immunoassays for binding, purifying, quantifying and otherwise generally detecting PDE protein components. As detailed below, immunoassays, in their most simple and direct sense, are binding assays. Certain preferred immunoassays are the various types of enzyme linked immunoadsorbent assays (ELISAs) and radioimmunoassays (RIA) known in the art. Immunohistochemical detection using tissue sections is also particularly useful. However, it will be readily appreciated that detection is not limited to such techniques, and Western blotting, dot and slot blotting, FACS analyses, and the like may also be used.

The steps of various useful immunoassays have been described in the scientific literature, such as, e.g., Nakamura et al., *In; Enzyme Immunoassays: Heterogeneous and Homogeneous Systems*, Chapter 27 (1987), incorporated herein by reference.

In general, the immunobinding methods include obtaining a sample suspected of containing a protein or peptide, in this case, cGMP-specific PDEs, and contacting the sample with a first antibody immunoreactive with cGMP-specific PDEs under conditions effective to allow the formation of immunocomplexes.

Immunobinding methods include methods for purifying PDE proteins, as may be employed in purifying protein from patients' samples or for purifying recombinantly expressed protein. They also include methods for detecting or quantifying the amount of a cGMP-specific PDE in a tissue sample, which requires the detection or quantification of any immune complexes formed during the binding process.

The biological sample analyzed may be any sample that is suspected of containing a cGMP-specific PDE such as a homogenized neoplastic tissue sample. Contacting the chosen biological sample with the antibody under conditions effective and for a period of time sufficient to allow the formation of immune complexes primary immune complexes) is generally a matter of adding the antibody composition to the sample and incubating the mixture for a period of time long enough for the antibodies to form immune complexes with, i.e., to bind to, any cGMP-specific PDEs present. The sample-antibody composition is washed extensively to remove any non-specifically bound antibody species, allowing only those antibodies specifically bound within the primary immune complexes to be detected.

In general, the detection of immunocomplex formation is well know art and may be achieved through the application of numerous approaches. These methods are based upon the detection of radioactive, fluorescent, biological or enzymatic tags. Of course, one may find additional advantages through the use of a secondary binding ligand such as a second antibody or a biotin/avidin ligand binding arrangement, as is known in the art.

The cGMP-specific PDE antibody used in the detection may itself be conjugated to a detectable label, wherein one would then simply detect this label. The amount of the primary immune complexes in the composition would, thereby, be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed extensively to remove any non-specifically bound labeled secondary antibodies or ligands, and the remaining label in the secondary immune complex is detected.

1. ELISAs

An enzyme linked immunoadsorbent assays (ELISAs) is a type of binding assay. In one type of ELISA, the cGMP-specific PDE antibodies used in the diagnostic method of this invention are immobilized onto a selected surface exhibiting protein affinity, such as a well in a polystyrene microtiter plate. Then, a suspected neoplastic tissue sample is added to the wells. After binding and washing to remove non-specifically bound immune complexes, the bound cGMP-specific PDE may be detected. Detection is generally achieved by the addition of another anti-PDE antibody that is linked to a detectable label. This type of ELISA is a simple "sandwich ELISA." Detection may also be achieved by the addition of a second anti-PDE antibody, followed by the addition of a third antibody that has binding affinity for the second antibody, with the third antibody being linked to a detectable label.

In another type of ELISA, the neoplastic tissue samples are immobilized onto the well surface and then contacted with the anti-PDE antibodies used in this invention. After binding and washing to remove non-specifically bound immune complexes, the bound cGMP-specific PDE antibodies are detected. Where the initial anti-PDE antibodies are linked to a detectable label, the immune complexes may be detected directly. Alternatively, the immune complexes may be detected using a second antibody that has binding affinity for the first anti-PDE antibody, with the second antibody being linked to a detectable label.

Irrespective of the format employed, ELISAs have certain features in common, such as coating, incubating or binding, washing to remove non-specifically bound species, and detecting the bound immune complexes.

2. RIAs

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various know concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector which counts the free antigen remaining in the sample. The antigen bound to the antibody or immunoadsorbent may also be similarly counted. Then, from the standard curve, the concentration of antigen in the original sample is determined.

D. Experimental Procedures

Cyclic GMP-binding cGMP-specific phosphodiesterase (cGB-PDE or PDE5) specifically hydrolyzes cGMP into 5'-GMP. It has two allosteric (non-catalytic) cGMP-binding sites located in the N-terminal region of the protein ($K_d$=1.3 mM), and a C-terminal catalytic domain which shows a strong preference for cGMP as a substrate ($K_m$=5.6 mM). Cyclic GMP-dependent protein kinase (PKG) specifically phosphorylates PDE5 at Serine-92 in the bovine sequence (Thomas, M. K. et al., J. Biol. Chem. 265: 14971–14978 (1990)). Generally, PDEs are difficult to express in their entirety in bacterial expression systems. There has been, however, greater success in the expression of recombinant proteins containing different functional domains of PDEs.

1. Antigen Production

Two polyclonal antibodies to PDE5 were produced. The glutathione-S-transferase (GST) fusion gene system (Pharmacia) was used to express a portion of the cGMP-binding domain of PDE5. Advantages of the GST expression system include its high yield and ease of purification of the GST fusion protein from bacterial lysates by affinity chromatography using Glutathione Sepharose 4B.

The first antibody, designated PDE5(1), was made using a short peptide of 17 amino acids as a hapten. The peptide sequence, CAQLYETSLLENKRNQV, corresponds to amino acids 307 to 322 of the cGMP high affinity binding domain of the bovine PDE5. (See, Beavo, et al., U.S. Pat. Nos. 5,652,131 and 5,702,936.) The peptide was synthesized using a Rainen Symphony Multiple Peptide Synthesizer, analyzed by mass spectrometry, and purified to greater than 90% purity using HPLC.

The peptide was synthesized to contain an N-terminal cysteine in order to produce a conjugated peptide. The purified peptide was linked via the sulfahydro of the N-terminal cysteine to maleimide-activated keyhole limpet hemocyanin (KLH, Pierce), yielding a KLH-PDE peptide conjugate.

A second polyclonal antibody, PDE5(2), was also prepared as a GST fusion protein. The antigen for PDE5(2) is designated PDE5cg. RT-PCR methods, discussed in greater detail below, were used to obtain the putative cGMP-binding domain of PDE5. Forward and reverse primers were designed to specifically amplify a region of the PDE5 cDNA sequence (McAllister-Lucas L. M., et al., J: Biol. Chem. 268, 22863–22873, 1993) and were not directed at conserved sequences among the PDE1–PDE7 families.

RNA from HT-29 cells was isolated using 5'-3', Inc. kits for total RNA preparation followed by oligo (dT) column purification of mRNA. The forward primer (GAA-TTC-CGT-CAC-AGC-CTT-ATG-TCA-C, corresponding to the bovine PDE5A cDNA sequence, nucleotides 561–579) and the reverse primer (CTC-GAG-TGC-ATC-ATG-TTC-CCT-TG, corresponding to the bovine PDE5A cDNA sequence, nucleotides 1264–1280) were used to obtain a 720 base pair fragment coding for the high affinity cGMP-binding domain of PDE5. The 720 base pair amplification product has 94% sequence homology with bovine PDE5 (nucleotides 561–1280) and codes for 240 amino acids with 98% similarity to the bovine amino acid sequence.

The 720 base pair fragment was cloned into the pGEX-5X-3 glutathione-S-transferase (GST) fusion vector (Pharmacia Biotech) using the EcoRI and XhoI restriction sites. The GST-fusion protein was expressed in E. coli BL21 cells under IPTG (100 μM) induction for 24 hrs. Then the fusion proteins were purified from the supernatant of the bacterial cell extract using a Glutathione Sepharose 4B affinity column and eluted with 10 mM reduced glutathione in 50 mM Tris-HCl (pH 8.0) according to the manufacturers instructions (GST Gene Fusion System, Pharmacia Biotech). Two milligrams of purified GST-cGMP binding domain fusion protein were obtained from one liter of bacterial culture. The GST-cGMP binding domain fusion protein yields a 56 KDa product on an SDS-PAGE gel.

The purified GST-PDE5 binding domain fusion protein is characterized by its cGMP specificity and its high affinity binding of cGMP. A cyclic GMP binding assay (Francis S. H., et al., J. Biol. Chem. 255, 620–626, 1980) was used to determine the $K_m$ of the fusion protein for cGMP. The assay was performed in a total volume of 100 μL containing 5 mM sodium phosphate buffer (pH 6.8), 1 mM EDTA and 0.25 mg/ml BSA and $H^3$-cGMP (5.8 Ci/mmol, NEN). The purified soluble GST-PDE5 binding domain fusion protein (5 to 50 μg/assay) was incubated at 22° C. for one hour and then transferred to a Brandel MB-24 Cell Harvester with GF/B as the filter membrane. Next the fusion protein was washed twice with 10 mL of cold 5 mM potassium buffer, pH 6.8. The membranes were cut out and transferred to scintillation vials, then 1 ml of $H_2O$ and 6 ml of Ready Safe liquid scintillation cocktail was added and the samples were counted on a Beckman LS 6500 scintillation counter. A $^3$H-cGMP saturation binding curve at 25° C. was generated. The GST-cGMP binding domain fusion protein displays one high affinity binding site for cGMP. The $K_m$ for cGMP is 0.41±0.08 μM, which is similar to the high affinity binding site of the bovine PDE5 ($K_d$=0.5 μM).

As a control, a blank sample was prepared by boiling the fusion protein for five minutes. The radioactivity detected for the boiled sample was less than one percent of that detected for the unboiled protein. The scintillation counting results were calibrated for quenching by filter membrane or other debris.

The fusion protein showed binding activity similar to that of the native enzyme. This includes specificity for cGMP over cAMP and 2'-substituted cyclic nucleotide analogs. These data suggest that the recombinant GST-cGMP binding domain fusion protein has high affinity cGMP binding characteristics similar to those of the cGMP binding site of PDE5.

2. Antibody Production

For the production of PDE5(1), sheep were injected with 100 μg of the KLH-conjugated peptide mixed with complete Freund's Adjuvant (Difco) for the initial injection. For subsequent injections, sheep were injected with the KLH-conjugated peptide mixed with incomplete Freund's Adjuvant every two weeks. Bleedings for antiserum were taken seven days after each injection, starting with the third injection. Pre-immunization serum was collected two weeks before antigen injection as a control for the antibody specificity assay. The test bleed was monitored by ELISA to determine the antibody titer.

The immunization procedure for preparation of the PDE5 (2) antibody was the same as that described above for the PDE5(1) antibody except 100 μg of affinity column purified GST-PDE5cg fusion protein (MW=56 KDa) was used as an antigen in each injection.

Immunoblots for human PDE5 were carried out by using PDE5(1) and PDE5(2) antisera from sheep. Pre-injection antiserum was used as a pre-immune control. Both PDE5(1) and PDE5(2) showed specific binding for the GST-cGMP binding fusion protein (56 KDa) and for the native PDE5 protein (~93 KDa) isolated from HT-29 cell extracts. As negative controls, pre-immune serum did not bind to these proteins and pre-incubation of the immune serum with an excess of the GST-cGMP binding domain fusion protein also blocked binding of the antibody to the PDE5 proteins. These results indicate that PDE5(1) and PDE5(2) antisera contain antibodies specific for human PDE5.

V. Nucleic Acid Detection

In another aspect, this invention includes the use of nucleic acid detection techniques to detect the level of cGMP-specific PDEs in a suspected neoplastic tissue sample. The nucleic acid sequences disclosed herein can be used in hybridization techniques such as slot and northern blots or in amplification techniques such as reverse transcriptase polymerase chain reaction (RT-PCR).

A. PCR Amplification

The level of cGMP-specific PDE mRNA in a neoplastic tissue sample can correspond to the level of expression of the protein. The presence of high levels of cGMP-specific PDE mRNA in a neoplastic tissue relative to normal tissue can indicate that the neoplasia will respond to treatment with a cGMP-specific PDE inhibitor.

Nucleic acid used as a template for amplification is isolated from suspected neoplastic tissue samples. The nucleic acid may be genomic DNA or whole cell or fractionated RNA. Methods of nucleic acid isolation are well know in the art. (See, e.g., Sambrook, et al., Molecular Cloning: A Laboratory Manual, 1989.)

In the diagnostic method if this invention, it is preferred that RNA is isolated from a tissue sample. The RNA can then further fractionated to isolate messenger RNA by selecting for polyadenylated RNA (poly-A RNA). Then the mRNA can be converted into complementary DNA (cDNA).

Briefly, in PCR, two oligonucleotide primers are synthesized whose sequences are complementary to sequences that are on opposite strands of the template DNA and flank the segment of DNA that is to be amplified. The template DNA is denatured by heating in the presence of an excess of the two primers, the four deoxynucleotide triphosphates, and magnesium. As the reaction is cooled, the primers anneal to their target sequences. Then the annealed primers are extended with DNA polymerase. The initial round can potentially double the product and each successive round of amplification can potentially lead to a logarithmic increase in amount of the amplification product because the product of one round can serve as template in the next round. Multiple rounds of amplification (denaturation, annealing, and DNA synthesis) are conducted until a sufficient amount of amplification product is produced. Finally, the amplification product is detected, usually by visual means or indirectly through chemiluminescence, or detection of a radioactive label or fluorescent label, or the like.

There are a number of template dependent amplification processes. One of the best known and most widely used is the polymerase chain reaction which is described in detail in U.S. Pat. Nos. 4,683,195, 4,683,202, and 4,800,159, which are incorporated herein by reference. The thermostable Taq DNA polymerase is most commonly used in the PCR process because it remains active at the high temperatures used in the amplification process.

Reverse transcriptase PCR (RT-PCR) can be used to estimate semiquantitative levels of mRNA of cGMP-specific PDEs in neoplastic tissue samples. Methods of reverse transcribing RNA into cDNA are well known and are described in Sambrook, et al., 1989.

B. Experimental Procedures

RNA was prepared from cells in culture or human and mouse tissue obtained from autopsy by using the QIAGEN (Valencia, Calif.) RNeasy Mini Kit. RNA then was treated with RNase-free DNase to eliminate genomic DNA contamination. cDNA was synthesized in a 30 μl reaction using 2 μg of total RNA. The RNA was heated for 5 minutes at 70° C. with random hexamers (Life Technologies, Inc.) and cooled on ice. Reverse transcription was performed at 42° C. for 1 hour with 0.5 mM dNTPs, 10 mM DTT, 1× reverse transcription buffer (Stratagene, La Jolla, Calif.), and 200 units of SuperScript II (Stratagene, La Jolla, Calif.) in the presence of RNase Inhibitors (Stratagene, La Jolla, Calif.). Seven percent of the cDNA was used for PCR amplification. PCR was performed for 30 cycles as follows: initial denaturation at 94° C. for 5 minutes, 94° C. for 1 minute, 55° C. for 2 minutes, 72° C. for 1 minute and extension at 72° C. for 7 minutes. PCR products were separated on a 1% agarose gel and electrophoresed in 1× TBE buffer. PCR products were purified using Geneclean (Bio 101, Inc.) and then sequenced.

Primers were synthesized to amplify a region of the human PDE5 mRNA which corresponds to the coding region for the N-terminal portion of the protein. The first set of primers, hV sense 1 and hV antisense 1 (s 1/as 1) generate a 385 base pair RT-PCR product which aligns with the human PDE5 sequence (Genbank accession #D 89094) from base pairs 432 to 816. Primers hV sense 2 and hV antisense 2 (s 2/as 2) generate a 174 base pair RT-PCR product which aligns with a human PDE5 splice variant, 5A2, (Genbank accession #Af043732) from base pairs 41 to 214.

Primer hV s 1: GGG ACT TTA CCT TCT CTT AC

Primer hV as 1: GTG ACA TCC AAG AAG TGA CTA GA

Primer hV s 2: CCC GAA GCC TGA GGA ATT GAT GC

Primer hV as 2: CTC CTC GAC CAT CAC TGC CG

VI. Diagnostic Kits

In another aspect, this invention provides for diagnostic kits for ascertaining whether a particular neoplasia is a type of neoplasia that would respond to treatment with a cGMP-specific PDE inhibitor. Diagnostic kits may be used to detect the level of mRNA encoding for cGMP-specific PDEs or the level of cGMP-specific PDE protein in a suspected neoplastic tissue sample.

The immunodetection kit includes an antibody or antibodies specifically reactive with cGMP-specific PDEs and an immunodetection reagent, and a means for containing each. The immunodetection reagent is most commonly an label associated with the antibody, or associated with a second binding ligand.

The nucleic acid detection kit includes an isolated cGMP-specific PDE nucleic acid segment or nucleic acid primers that hybridize to distant sequences of a cGMP-specific PDE, capable of amplifying a nucleic acid segment of a cGMP-specific PDE.

Such kits are used to detect the amount of cGMP-specific PDE protein or mRNA, respectively, in a neoplastic tissue sample. The detection of elevated amounts of cGMP-specific PDE protein or mRNA in a neoplastic tissue relative to normal tissue is indicative that the neoplasia has potential for being treated by a cGMP-specific PDE inhibitor.

VII. The Novel cGMP-specific Phosphodiesterase

As mentioned above, a new cyclic GMP-specific phosphodiesterase has been discovered in neoplastic cells. Treatment of cells with a compound that inhibits both PDE5 and this novel cGMP-specific PDE leads to apoptosis of the neoplastic cells, as described below.

The new PDE is broadly characterized by:
(a) cGMP specificity over cAMP;
(b) positive cooperative kinetic behavior in the presence of cGMP substrate;
(c) submicromolar affinity for cGMP; and
(d) insensitivity to incubation with purified cGMP-dependent protein kinase.

As discussed below, this new cGMP-PDE is unique from the previously-characterized PDE5. Kinetic data reveal that the new PDE has increased cGMP hydrolytic activity in the presence of increasing cGMP substrate concentrations, unlike PDE5 which exhibits cGMP substrate saturation. The new cGMP-PDE is insensitive to incubation with cGMP-dependent protein kinase (PKG), whereas PDE5 is phosphorylated by PKG. Additionally, the new cGMP-PDE is relatively insensitive to inhibition with the PDE5-specific inhibitors, zaprinast, E4021, and sildenafil. Finally, the new cGMP-PDE activity can be separated from the previously-characterized PDE5 activity by anion-exchange chromatography.

The new cGMP-PDE is not a member of any of the other previously characterized PDE families. The new PDE does not hydrolyze cAMP significantly. Calcium (with or without calmodulin) fails to activate either cAMP or cGMP hydrolysis activity, indicating that the novel PDE is not a CaM-PDE (PDE1). Additionally, cGMP failed to activate or inhibit cAMP hydrolysis, indicating that the new cGMP-PDE it is not a cGMP-stimulated PDE (cGS-PDE or PDE2), because all known isoforms of the PDE2 family hydrolyze both cAMP and cGMP. Further, the new cGMP-PDE is insensitive to a number of specific PDE inhibitors. It is relatively insensitive to vinpocetine (a CaM-PDE- or PDE1-specific inhibitor), to indolodan (a cGI-PDE- or PDE3-specific inhibitor), and to rolipram (a cAMP-PDE- or PDE4-specific inhibitor). These data establish that the new PDE is not one of the previously known cAMP-hydrolyzing PDEs (PDE1, PDE2, PDE3, or PDE4).

The cGMP-specific PDE inhibitors that are preferable for treating patients with neoplasia inhibit both PDE5 and the new cGMP-PDE. A compound that inhibits both forms of cGMP-specific PDE is desirable because a compound that inhibits PDE5 but not the new PDE, does not by itself induce apoptosis. For example, zaprinast, sildenafil, and E4021 have been reported as potent inhibitors of PDE5. (See, e.g., Loughney K., et al., *Gene* 216(1):139–47, 1998.) However, compared to PDE5, the new PDE is relatively insensitive to zaprinast, sildenafil, and E4021 (Table 5, below). And none of the three, zaprinast, sildenafil, or E4021, have been found to induce apoptosis or to inhibit cell growth in neoplastic cells.

However, a number of PDE5 inhibitors have been found to induce apoptosis in neoplastic cells. Examples of such compounds are sulindac sulfide and Compound E. Compound E is defined as [(Z)-5-fluoro-2-methyl-1-(3,4,5-trimethoxybenzylidene)-3-indenylacetamide, N-benzyl]. Sulindac sulfide and Compound E each inhibit PDE5 and the new cGMP-PDE (Table 5, below). And both sulindac sulfide and Compound E induce apoptosis in neoplastic cells. Compounds that inhibit PDE5, but not the new cGMP-PDE, have not been shown to cause apoptosis in neoplastic cells. But compounds that inhibit both PDE5 and the new cGMP-PDE have been found to induce apoptosis in neoplastic cells.

A. Isolation of the Novel cGMP-specific Phosphodiesterase

The novel cGMP-specific phosphodiesterase can be isolated from human carcinoma cell lines (e.g. SW480, a human colon cancer cell line that originated from a moderately differentiated epithelial adenocarcinoma, available from the American Tissue Type Collection in Rockville, Md. U.S.A.). The isolation of this new cGMP-PDE is described in issued U.S. Pat. No. 6,200,771 (Case No. P-143).

Figure 3:
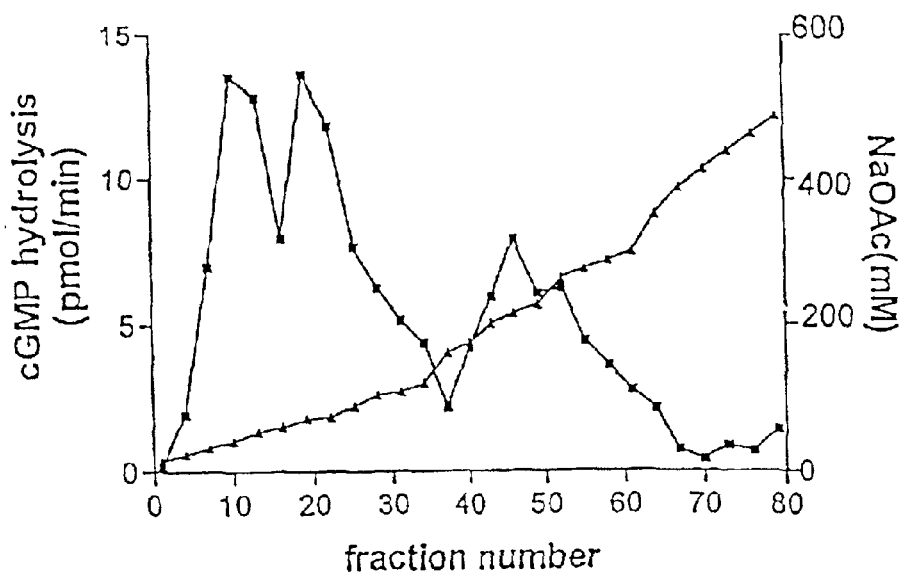
FIG. 3 is a graph of the cGMP activities of the cGMP phosphodiesterases obtained from SW-480 neoplastic cells, as assayed from the eluent from a DEAE-Trisacryl M column.

Briefly, to isolate the novel phosphodiesterase, SW-480 cells are collected and homogenized. The homogenate is centrifuged, and the supernatant is loaded onto a DEAE-Trisacryl M column. The loaded column is then washed, and PDE activities are eluted with a linear gradient of NaOAc. Fractions are collected and immediately assayed for cGMP hydrolysis activity. Cyclic nucleotide PDE activity of each fraction is determined using the modified two-step radioisotopic method of Thompson, et al., (Thompson W. J., et al., *Adv Cyclic Nucleotide Res* 10: 69–92, 1979). There are two initial peaks of cGMP-PDE activity eluted from the column, peak A and peak B (see FIG. 3). Peak A is PDE5, whereas peak B is the new cGMP-PDE.

Figure 4:
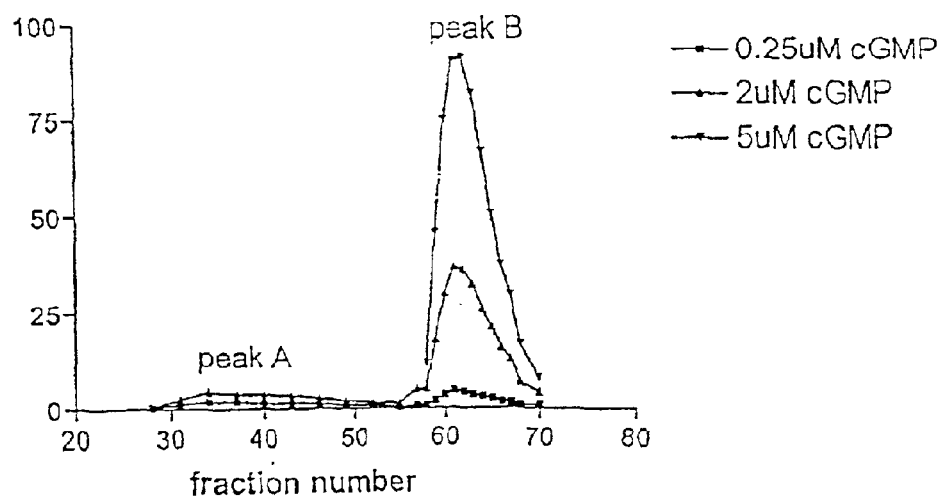
FIG. 4 is a graph of cGMP activities of the reloaded cGMP phosphodiesterases obtained from SW-480 neoplastic cells, as assayed from the eluent from a DEAE-Trisacryl M column.

To fractionate the cGMP hydrolytic activity of PDE5 and the new cGMP-PDE further, the fractions containing those activities are reloaded onto the DEAE-Trisacryl M column and eluted with a linear gradient of NaOAc. Fractions are again immediately assayed for cGMP hydrolysis activity, the results of which are illustrated in FIG. 4. FIG. 4 shows that peak B, the novel PDE, exhibits enhanced activity with increasing cGMP substrate concentration. Peak A, on the other hand, shows apparent substrate saturation with increasing concentrations of cGMP.

B. cGMP-Specificity of PDE Peaks A and B

Each fraction from the DEAE column was also assayed for cGMP-hydrolysis activity (0.25 $\mu$M cGMP) in the presence or absence of $C^{++}$, or $C^{++}$-CaM and/or EGTA and for cAMP (0.25 $\mu$M cAMP) hydrolysis activity in the presence or absence of 5 $\mu$M cGMP. Neither PDE peak A nor peak B (fractions 5–22; see FIG. 3) hydrolyzed cAMP significantly, establishing that neither was a member of a cAMP hydrolyzing family of PDEs (i.e., a PDE1, 2, 3).

$Ca^{++}$ (with or without calmodulin) failed to activate either cAMP or cGMP hydrolysis activity of either peak A or B, and cGMP failed to activate or inhibit cAMP hydrolysis. Such results establish that peaks A and B constitute cGMP-specific PDEs but not PDE1, PDE2, PDE3, or PDE4.

For PDE peak B, as discussed below, cyclic GMP activated the cGMP hydrolytic activity of the enzyme, but did not activate any cAMP hydrolytic activity. This reveals that PDE peak B—the novel phosphodiesterase—is not a cGMP-stimulated cyclic nucleotide PDE ("cGS") or among the PDE2 family isoforms because the known isoforms of PDE2 hydrolyze both cGMP and cAMP.

C. Peak a is a PDE5, but Peak B—a New cGMP-specific PDE—is Not

To characterize any PDE isoform, kinetic behavior and substrate preference should be assessed. Peak A showed typical "PDE5" characteristics. For example, the $K_m$ of the enzyme for cGMP was 1.07 $\mu M$, and Vmax was 0.16 nmoL/min/mg. In addition, as discussed below, zaprinast ($IC_{50}$=1.37$\mu M$), E4021 ($IC_{50}$=3 nM), and sildenafil inhibited activity of peak A. Further, zaprinast showed competitive inhibition for cGMP hydrolysis activity of peak A, consistent with results reported in the literature for PDE5.

Figure 5:
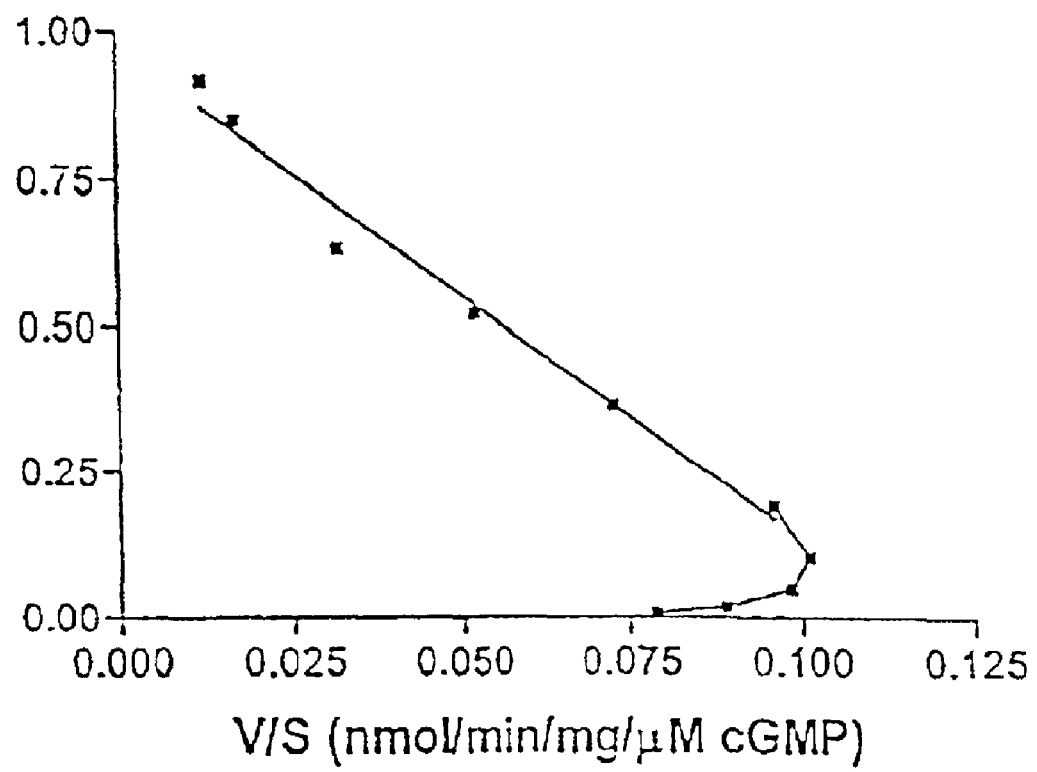
FIG. 5 is a graph of the kinetic behavior of the novel PDE.

PDE peak B showed considerably different kinetic properties as compared to PDE peak A. For example, in Eadie-Hofstee plots of peak A, cyclic GMP hydrolysis shows a single line with negative slope with increasing substrate concentrations, indicative of Michaelis-Menten kinetic behavior. Peak B, however, shows the novel property for cGMP hydrolysis in the absence of cAMP of a decreasing (apparent $K_m$=8.4), then increasing slope ($K_m$<1) of Eadie-Hofstee plots with increasing cGMP substrate (see FIG. 5). This establishes peak B's submicromolar affinity for cGMP (i.e., where $K_m$<1).

Consistent with the kinetic studies (i.e., FIG. 5) and positive-cooperative kinetic behavior in the presence of cGMP substrate, is the increased cGMP hydrolytic activity in the presence of increasing concentrations of cGMP substrate. This was discovered by comparing 0.25 $\mu M$, 2 $\mu M$, and 5 $\mu M$ concentrations of cGMP in the presence of PDE peak B after a second DEAE separation to rule out cAMP hydrolysis and to rule out this new enzyme being a "classic" PDE5. Higher cGMP concentrations evoked disproportionately greater cGMP hydrolysis with PDE peak B, as shown in FIG. 4.

These observations suggest that cGMP binding to the peak B enzyme causes a conformational change in the enzyme.

D. Zaprinast- and Sildenafil-insensitivity of PDE Peak B Relative to Peak A, and Their Effects on Other PDE Inhibitors Different PDE inhibitors were studied using twelve concentrations of drug from 0.01 $\mu M$ to 100 $\mu M$ and a substrate concentration of 0.25 $\mu M$ $^3$H-cGMP. $IC_{50}$ values were calculated with variable slope, sigmoidal curve fits using Prism 2.01 (GraphPad). The results are shown in Table 5, below. While compounds E4021 and zaprinast inhibited peak A, (with high affinities) $IC_{50}$ values calculated against peak B are significantly increased (>50 fold). This confirms that peak A is a PDE5. These data further illustrate that the novel PDE is, for all practical purposes, zaprinast-insensitive and E4021-insensitive.

TABLE 5

Comparison of PDE Inhibitors Against Peak A and Peak B (cGMP Hydrolysis)

| Compound | PDE Family Inhibitor | $IC_{50}$ Peak A ($\mu M$) | $IC_{50}$ Peak B ($\mu M$) | Ratio ($IC_{50}$ Peak A/ Peak B) |
|---|---|---|---|---|
| E4021 | 5 | 0.003 | 8.4 | 0.0004 |
| Zaprinast | 5 | 1.4 | >30 | <0.05 |
| Compound E | 5 and others | 0.38 | 0.37 | 1.0 |

TABLE 5-continued

Comparison of PDE Inhibitors Against Peak A and Peak B (cGMP Hydrolysis)

| Compound | PDE Family Inhibitor | $IC_{50}$ Peak A ($\mu M$) | $IC_{50}$ Peak B ($\mu M$) | Ratio ($IC_{50}$ Peak A/ Peak B) |
|---|---|---|---|---|
| Sulindac sulfide | 5 and others | 50 | 50 | 1.0 |
| Vinpocetine | 1 | >100 | >100 | |
| EHNA | 2, 5 | >100 | 3.7 | |
| Indolidan | 3 | 31 | >100 | <0.31 |
| Rolipram | 4 | >100 | >100 | |
| Sildenafil | 5 | .0003 | >10 | <.00003 |

By contrast, sulindac sulfide and Compound E competitively inhibit both peak A and peak B phosphodiesterases at the same potency (for Compound E, $IC_{50}$=0.38 $\mu M$ for PDE peak A; $IC_{50}$=0.37 $\mu M$ for PDE peak B).

There is significance for the treatment of neoplasia and the selection of cGMP-specific PDE inhibitors for such treatment in the fact that peak B is zaprinast-insensitive whereas peaks A and B are both sensitive to sulindac sulfide and Compound E. Zaprinast, E4021, and sildenafil have been tested to ascertain whether they induce apoptosis or inhibit the growth of neoplastic cells, and the same has been done for Compound E. Zaprinast, sildenafil and E4021 do not have significant apoptosis-inducing or growth-inhibiting properties, whereas sulindac sulfide and Compound E are precisely the opposite. In other words, the ability of a compound to inhibit both PDE peaks A and B correlates with its ability to induce apoptosis in neoplastic cells, whereas if a compound (e.g., zaprinast) has specificity for PDE peak A only, that compound will not induce apoptosis.

E. Insensitivity of PDE Peak B to Incubation with cGMP-dependent Protein Kinase

Further differences between PDE peaks A and B were observed in their respective cGMP-hydrolytic activities in the presence of varying concentrations of cGMP-dependent protein kinase (PKG, which phosphorylates typical PDE5). Specifically, peak A and peak B fractions were incubated with different concentrations of protein kinase G at 30° C. for 30 minutes. Cyclic GMP hydrolysis of both peaks was assayed after phosphorylation was attempted. Consistent with previously published information about PDE5, peak A showed increasing cGMP hydrolysis activity in response to protein kinase G incubation, indicating that peak A was capable of being phosphorylated. Peak B was unchanged, however (i.e., was not capable of being phosphorylated and was insensitive to incubation with cGMP-dependent protein kinase). These data are consistent with peak A being a PDE5 family isoform and peak B being a novel cGMP-specific PDE.

Obviously, numerous modifications and variations of the present invention are possible in light of the above teachings. It is therefore to be understood that within the scope of the appended claims, the invention may be practiced otherwise than as specifically described herein.

We claim:

1. A method for identifying neoplasias responsive to treatment with compounds that selectively inhibit cGMP-specific PDE activity, comprising (a) removing a sample of neoplastic tissue from a patient, (b) growing cells from the sample as explants in vitro, (c) contacting a sample of said cells with a compound that has cGMP-specific PDE inhibition activity, (d) comparing the growth of the cells in the presence of the compound with the growth of cells in the absence of the compound, and (e) determining whether the growth of the neoplasia is sensitive to inhibition by the compound.

2. A method for identifying neoplasias responsive to treatment with a cGMP-specific PDE inhibitor comprising determining the level of cGMP-specific PDEs in a sample of neoplastic tissue, wherein an elevated level of cGMP-specific PDEs in the neoplastic tissue, relative to normal tissue, is indicative that the neoplasia has potential for being treated by a cGMP-specific PDE inhibitor.

3. The method of claim 2, wherein the determination of the level of cGMP-specific PDEs in the neoplastic tissue comprises determining the amount of cGMP-specific PDE protein in the neoplastic tissue sample.

4. The method of claim 2, wherein the determination of the level of cGMP-specific PDEs in the neoplastic tissue comprises determining the amount of mRNA encoding for GMP-specific PDEs in the neoplastic tissue sample.

5. The method of claim 2, wherein the determination of the level of cGMP-specific PDEs in the neoplastic tissue comprises determining the cGMP hydrolytic activity of GMP-specific PDEs in the neoplastic tissue sample.

6. A method for identifying neoplasias responsive to treatment with compounds that selectively inhibit cGMP-specific PDE activity, comprising (a) removing a sample of neoplastic tissue from a patient, (b) growing cells from the sample as explants in vitro, (c) contacting a sample of said cells with a compound that has cGMP-specific PDE inhibition activity, (d) comparing the number of apoptotic cells in the presence of the compound with the number of apoptotic cells in the absence of the compound, and (e) determining whether the compound promoter an increase in apoptosis in the neoplasia.

* * * * *